United States Patent
Otomaru et al.

(10) Patent No.: US 11,311,259 B2
(45) Date of Patent: Apr. 26, 2022

(54) IMAGE PROCESSING APPARATUS, IMAGE PROCESSING METHOD, AND COMPUTER-READABLE MEDIUM

(71) Applicant: CANON KABUSHIKI KAISHA, Tokyo (JP)

(72) Inventors: Itaru Otomaru, Kawasaki (JP); Takaaki Endo, Urayasu (JP)

(73) Assignee: Canon Kabushiki Kaisha, Tokyo (JP)

( * ) Notice: Subject to any disclaimer, the term of this patent is extended or adjusted under 35 U.S.C. 154(b) by 130 days.

(21) Appl. No.: 16/821,000

(22) Filed: Mar. 17, 2020

(65) Prior Publication Data
US 2020/0214658 A1    Jul. 9, 2020

Related U.S. Application Data

(63) Continuation of application No. PCT/JP2018/034882, filed on Sep. 20, 2018.

(30) Foreign Application Priority Data

Sep. 29, 2017  (JP) .............................. JP2017-190959
Sep. 20, 2018  (JP) .............................. JP2018-176153

(51) Int. Cl.
*G06K 9/00*    (2006.01)
*A61B 6/00*    (2006.01)
(Continued)

(52) U.S. Cl.
CPC ................ *A61B 6/466* (2013.01); *A61B 6/03* (2013.01); *A61B 6/5211* (2013.01); *G06T 7/35* (2017.01);
(Continued)

(58) Field of Classification Search
CPC ......... A61B 6/466; A61B 6/5211; A61B 6/03; G06T 15/08; G06T 15/20;
(Continued)

(56) References Cited

U.S. PATENT DOCUMENTS 8,542,891 B2    9/2013  Yokota et al.
9,053,565 B2 *  6/2015  Buelow .................. G06T 19/00
(Continued)

FOREIGN PATENT DOCUMENTS

CN    101617943 A    1/2010
JP    2010-029641 A   2/2010
(Continued)

OTHER PUBLICATIONS

Yoshinobu Sato, et al., "Tissue Classification Based on 3D Local Intensity Structures for Volume Rendering," IEEE Transactions on Visualization and Computer Graphics, vol. 6, No. 2, Apr.-Jun. 2000, pp. 160-177.
(Continued)

*Primary Examiner* — Shervin K Nakhjavan
(74) *Attorney, Agent, or Firm* — Venable LLP

(57) ABSTRACT

The image processing apparatus acquires a first three-dimensional image, generates a second three-dimensional image by applying image processing to the first three-dimensional image having been acquired, and generates a two-dimensional projected image by applying projection processing to the second three-dimensional image having been generated. The image processing apparatus determines a parameter to be used for the image processing of the three-dimensional image on the basis of a parameter for the projection processing.

20 Claims, 7 Drawing Sheets

(51) Int. Cl.
  *A61B 6/03* (2006.01)
  *G06T 15/08* (2011.01)
  *G06T 15/20* (2011.01)
  *G06T 7/35* (2017.01)
  *G06T 11/00* (2006.01)

(52) U.S. Cl.
  CPC ............ *G06T 11/008* (2013.01); *G06T 15/08* (2013.01); *G06T 15/20* (2013.01); *G06T 2207/10081* (2013.01); *G06T 2207/30068* (2013.01); *G06T 2210/41* (2013.01); *G06T 2211/40* (2013.01)

(58) Field of Classification Search
  CPC . G06T 2207/30068; G06T 2207/10081; G06T 2210/41; G06T 2211/40
  See application file for complete search history.

(56) References Cited

U.S. PATENT DOCUMENTS

| | | | |
|---|---|---|---|
| 9,147,280 B2 | 9/2015 | Murphy et al. | |
| 9,280,822 B2* | 3/2016 | Fan | G06T 7/11 |
| 9,984,478 B2* | 5/2018 | Westerhoff | G06T 11/008 |
| 10,304,158 B2 | 5/2019 | Endo et al. | |
| 10,366,544 B2 | 7/2019 | Endo et al. | |
| 10,548,483 B2 | 2/2020 | Endo et al. | |
| 2005/0171430 A1* | 8/2005 | Zhang | A61B 8/13 |
| | | | 600/437 |
| 2007/0008318 A1* | 1/2007 | Matsumoto | G06T 15/08 |
| | | | 345/424 |
| 2010/0002839 A1 | 1/2010 | Yokota et al. | |
| 2010/0316277 A1* | 12/2010 | Fan | G06T 7/187 |
| | | | 382/131 |
| 2011/0019890 A1* | 1/2011 | Oikawa | A61B 6/469 |
| | | | 382/131 |
| 2011/0037761 A1* | 2/2011 | Mistretta | A61B 6/4441 |
| | | | 345/419 |
| 2011/0235890 A1* | 9/2011 | Ruijters | G06T 3/0068 |
| | | | 382/132 |
| 2013/0222383 A1* | 8/2013 | Taniguchi | A61B 6/466 |
| | | | 345/424 |
| 2014/0035916 A1 | 2/2014 | Murphy et al. | |
| 2014/0185896 A1* | 7/2014 | Baturin | A61B 6/5217 |
| | | | 382/131 |
| 2015/0104091 A1* | 4/2015 | Miyasa | G06T 3/0068 |
| | | | 382/131 |
| 2015/0243055 A1* | 8/2015 | Nishiyama | G06T 19/20 |
| | | | 382/131 |
| 2015/0279120 A1* | 10/2015 | Sakuragi | G06T 19/003 |
| | | | 382/103 |
| 2016/0035102 A1 | 2/2016 | Jerebko | |
| 2016/0048984 A1* | 2/2016 | Frigo | G06T 15/08 |
| | | | 382/131 |
| 2016/0287201 A1* | 10/2016 | Bergtholdt | A61B 6/5223 |
| 2016/0317027 A1* | 11/2016 | Goto | A61B 3/102 |
| 2016/0371860 A1* | 12/2016 | Liu | G06T 11/003 |
| 2017/0124766 A1* | 5/2017 | Takama | G06T 15/08 |
| 2017/0164908 A1* | 6/2017 | Kimura | A61B 5/7282 |
| 2018/0286108 A1* | 10/2018 | Hirakawa | G06T 15/205 |
| 2019/0102932 A1 | 4/2019 | Naganawa et al. | |
| 2019/0311549 A1 | 10/2019 | Endo et al. | |

FOREIGN PATENT DOCUMENTS

| | | |
|---|---|---|
| JP | 2014-030693 A | 2/2014 |
| JP | 2017-108789 A | 6/2017 |

OTHER PUBLICATIONS

Dec. 4, 2018 International Search Report in International Patent Appln. No. PCT/JP2018/034882.

* cited by examiner

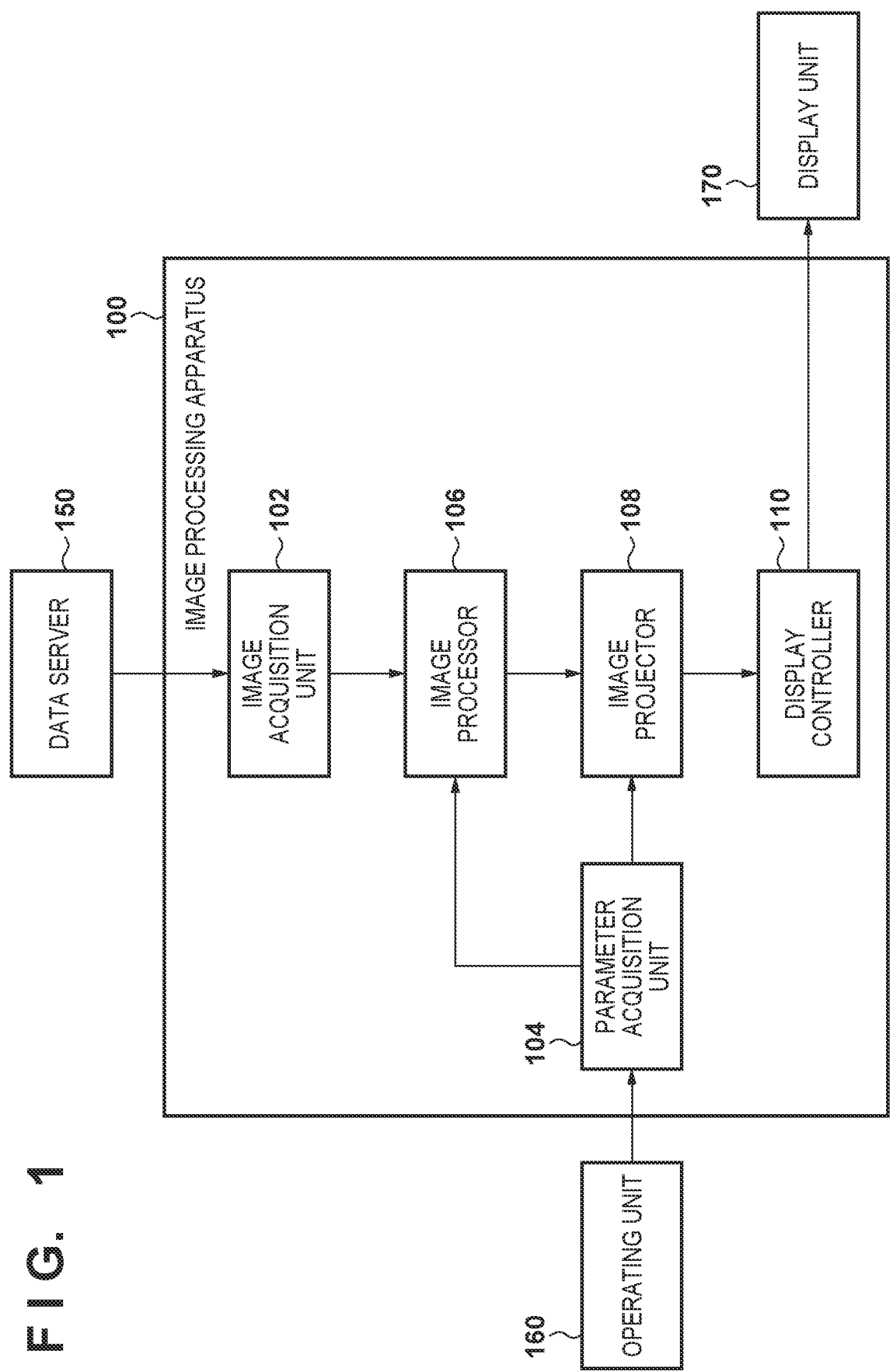

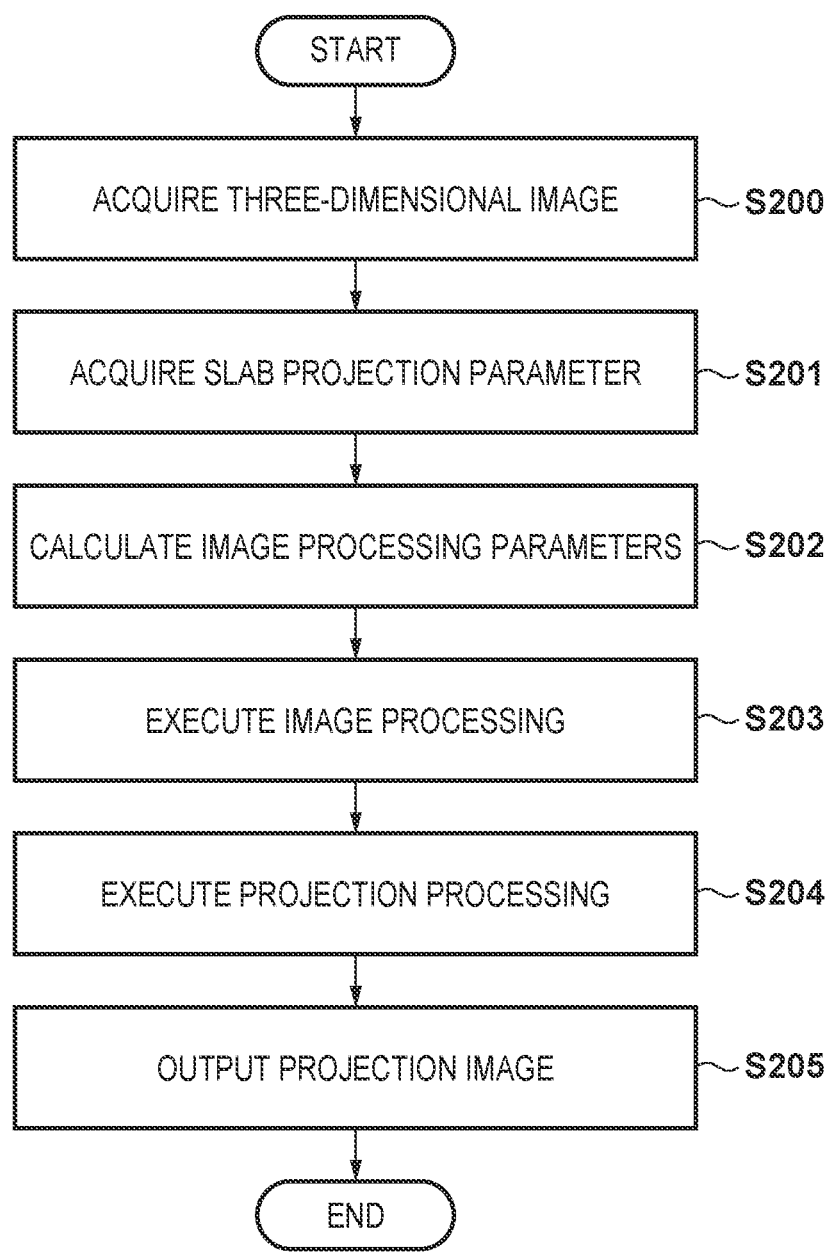

IMAGE PROCESSING APPARATUS, IMAGE PROCESSING METHOD, AND COMPUTER-READABLE MEDIUM

CROSS-REFERENCE TO RELATED APPLICATIONS

This application is a Continuation of International Patent Application No. PCT/JP2018/034882, filed Sep. 20, 2018, which claims the benefit of Japanese Patent Application No. 2017-190959, filed Sep. 29, 2017, and Japanese Patent Application No. 2018-176153, filed Sep. 20, 2018, all of which are hereby incorporated by reference herein in their entirety.

BACKGROUND OF THE INVENTION

Field of the Invention

The present invention relates to an image processing apparatus and an image processing method for generating a two-dimensional projection image from a three-dimensional image captured by an imaging apparatus (modality).

Background Art

In the field of medicine, imaging apparatuses (modalities), such as three-dimensional CT imaging apparatuses and Mill apparatuses, have been developed that can acquire high-definition three-dimensional images of subjects. In comparison with conventional two-dimensional images represented by plain X-ray images, the number of three-dimensional images to be read by a medical practitioner is large. Therefore, there is a need for an image displaying method that enables ready identification of a three-dimensional structure of a subject without significantly increasing the reading time, and makes better reading possible.

Various types of projection display, such as maximum intensity projection (MIP) and volume rendering, are typically used to identify the three-dimensional structure of a subject in a single display image. In particular, "slab projection" that limits the projection range to a certain thickness is performed in some cases in which a target region, such as a lesion, is to be examined through projection display. In such slab projection, the projection range is referred to as the slab thickness. PTL 1 discloses a technique for slab projection in which pre-calculation is used to shorten the calculation time required for projection calculation.

CITATION LIST

Patent Literature

PTL 1: Japanese Patent Laid-Open No. 2014-30693

Non Patent Literature

NPL 1: Sato Y. et al., Tissue Classification Based on 3D Local Intensity Structures for Volume Rendering. IEEE Trans Vis Computer Graphics 6:160-177, 2000.

However, the method described in PTL 1 has an issue in that, when a projection parameter (for example, slab thickness) is changed during projection display, there are cases where the visibility of the target region is decreased.

SUMMARY OF THE INVENTION

According to an embodiment of the present invention, there is provided an image processing apparatus that enhances the visibility of an image generated from a three-dimensional image.

According to one aspect of the present invention, there is provided an image processing apparatus comprising: a first acquiring unit configured to acquire a first three-dimensional image; an image processing unit configured to generate a second three-dimensional image by applying image processing to the first three-dimensional image; a projecting unit configured to generate a two-dimensional projection image by applying projection processing to the second three-dimensional image; and a determining unit configured to determine a parameter of the image processing based on a parameter related to the projection processing.

According to another aspect of the present invention, there is provided an image processing apparatus comprising: a first acquiring unit configured to acquire a first three-dimensional image; a projecting unit configured to generate a two-dimensional first projection image by subjecting the first three-dimensional image to projection processing; and an image processing unit configured to determine a parameter related to image processing performed on the first three-dimensional image based on a feature amount of the first projection image.

According to another aspect of the present invention, there is provided an image processing method for processing a three-dimensional image, the method comprising: acquiring a first three-dimensional image; generating a second three-dimensional image by subjecting the first three-dimensional image to image processing; and generating a two-dimensional projection image by subjecting the second three-dimensional image to projection processing, wherein a parameter of the image processing is determined based on a parameter related to the projection processing.

According to another aspect of the present invention, there is provided an image processing method for processing a three-dimensional image, the method comprising: acquiring a three-dimensional image; generating a two-dimensional projection image by subjecting the three-dimensional image to projection processing; and determining a parameter related to image processing performed on the three-dimensional image based on a feature amount of the projection image.

Further features of the present invention will become apparent from the following description of exemplary embodiments with reference to the attached drawings.

BRIEF DESCRIPTION OF THE DRAWINGS

The accompanying drawings are included in, and form part of, the specification, illustrate embodiments of the present invention, and together with the description thereof, are used to describe the principles of the invention.

FIG. 1 is a block diagram illustrating a functional configuration example of an image processing apparatus according to a first embodiment.

FIG. 2 is a flowchart illustrating an overall processing procedure according to the first embodiment.

DESCRIPTION OF THE EMBODIMENTS

Figure 3A:
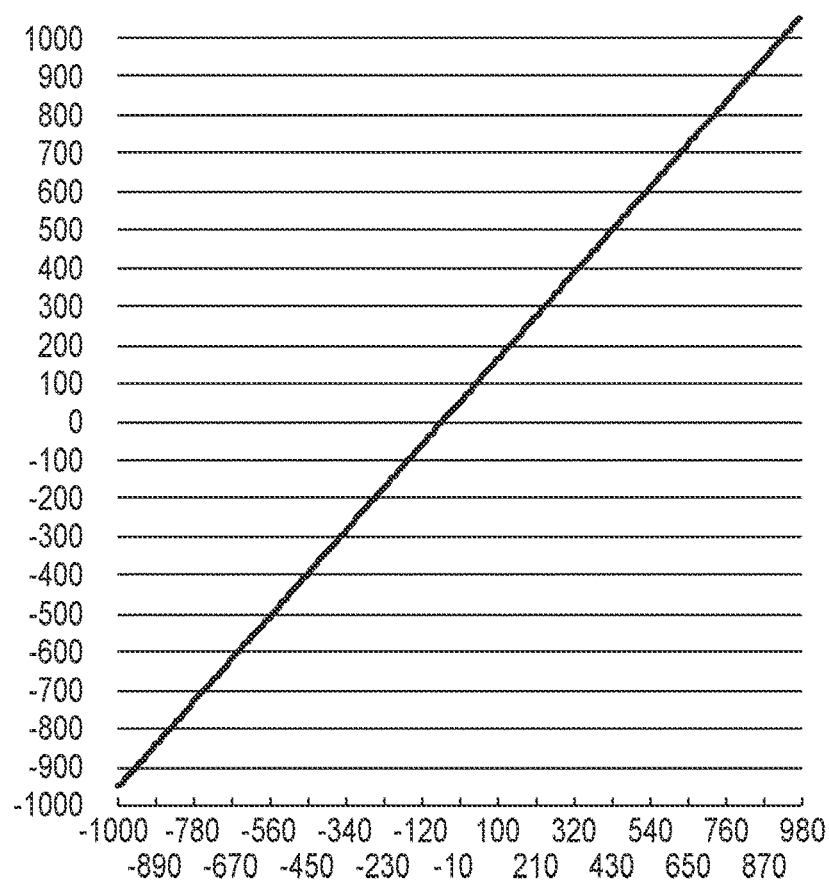
FIG. 3A is a diagram illustrating a density-value conversion function during low-density-region reduction processing.

Embodiments of the present invention will now be described in detail with reference to the accompanying drawings. However, the scope of the invention is not limited to the illustrated examples.

First Embodiment

An image processing apparatus according to the first embodiment adjusts parameters for three-dimensional image processing in accordance with the slab thickness used in the two-dimensional projection processing, and thereby enhances the visibility of a target region. In the first embodiment, a case in which a three-dimensional CT image of a breast region (hereinafter, referred to as "breast CT image") is captured by an X-ray CT apparatus will be described as an example. Note that, in the description below, a target region in a breast CT image refers to a tumor region.

An issue that is a premise of the first embodiment will now be described in detail. In reading of a breast CT image, a two-dimensional projection image (hereinafter, simply referred to as "projection image") is calculated and displayed using a ray summation projection method (hereinafter, referred to as "RaySum projection"), which is a known projection technique. RaySum projection is a projection method in which the sum of density values on a projection path leading to one pixel in a projection image is defined as the density value of the pixel in the projection image. By using RaySum projection, it is possible to examine the shading required for reading, such as the outline of a tumor region, which is the target region, and architectural distortion of the surrounding tissue. However, in RaySum projection, if the difference in the contrast between the tumor region and the surrounding region is low in the pre-projection three-dimensional image, the contrast of the projection image will be low when a slab thickness larger than a certain value (for example, 5 mm or larger in the case of a breast CT image) is set, and thus it is difficult to examine the tumor region.

To solve the above-described issue, the first embodiment takes an approach of increasing the contrast between the tumor region and the surrounding region by performing image processing (gradation processing) to reduce or enhance a predetermined density region in a three-dimensional image before projection processing is performed. Since the density of the surrounding region is lower than the density of the tumor region, gradation processing can be used to reduce the low-density region (surrounding region) or enhance the high-density region (tumor region). In the first embodiment, the contrast between the tumor region and the surrounding region is increased through gradation processing that reduces the density value of the surrounding region (low-density region). Hereinafter, this processing is referred to as "low-density region reduction processing". Details of the low-density-region reduction processing will be described in the description of step S202 (FIG. 2). By carrying out the low-density-region reduction processing, the contrast of the projection image can be maintained even when the slab thickness is set to a large value. On the other hand, in the case of projection not being performed (display of a slice) or a small slab thickness, the result may be an unnatural image having an excessively large contrast. This embodiment solves the above-described issue by decreasing the effect of the low-density-region reduction processing when no projection is performed or when the slab thickness is smaller than or equal to a certain value and increasing the effect of the low-density-region reduction processing when the slab thickness is larger than a certain value. In this way, the image processing apparatus according to this embodiment is able to provide a projection image having a favorable contrast even when the slab thickness is changed.

Figure 7:
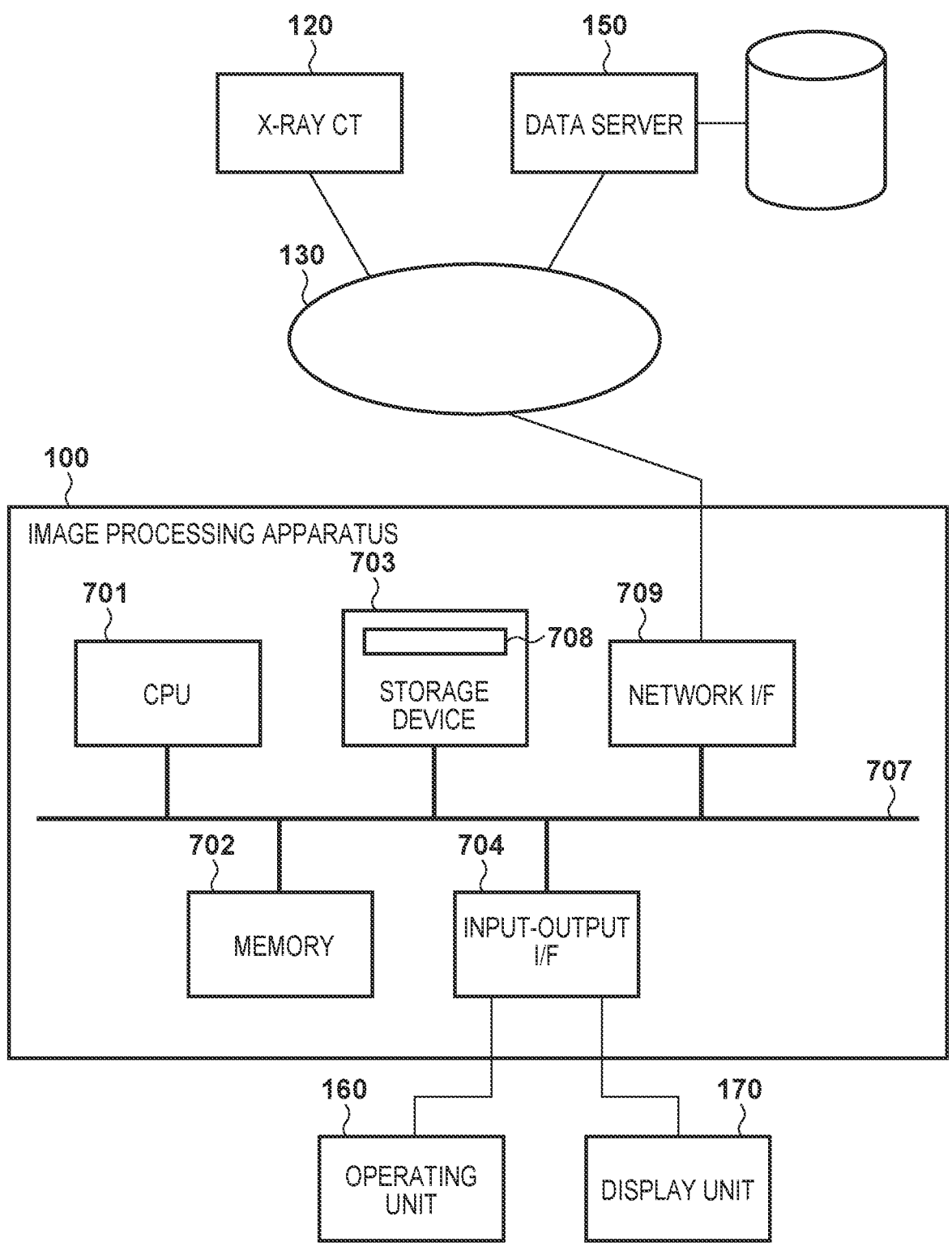
FIG. 7 is a diagram illustrating a hardware configuration example of an image processing apparatus and a configuration example of an image processing system.

The configuration and processes according to the first embodiment will now be described with reference to FIGS. 1 to 4A, 4B, and 7. FIG. 7 is a diagram illustrating a hardware configuration example of an image processing apparatus and a configuration example of an image processing system according to the first embodiment. In the image processing system according to this embodiment, an X-ray CT apparatus 120, which is an example of a modality for acquiring a three-dimensional image, a data server 150 that stores and manages the three-dimensional image acquired by the X-ray CT apparatus 120, and an image processing apparatus 100 are connected to a network 130. The image processing apparatus 100 includes a CPU 701, a memory 702, a storage device 703, an input-output interface 704, and a network interface 709, and these components are mutually connected via a bus 707. Note that the data server 150 and the image processing apparatus 100 may be directly connected to each other without being connected to each other via the network 130. Alternatively, the image processing apparatus 100 may have the function of the data server 150.

The CPU 701 of the image processing apparatus 100 executes a program 708 stored in the storage device 703 so as to execute various functions. The memory 702 temporarily stores programs and data read from the storage device 703 by the CPU 701. Moreover, the memory 702 is also used as a work area by the CPU 701 to execute various programs. The storage device 703 stores an operating system (OS), various programs, control programs, data, and the like. Note that the program 708 for control is stored as a portion of the data of the storage device 703. The CPU 701 realizes various controls of the image processing apparatus 100 by executing the program 708. For example, the functions and processes of the image processing apparatus 100 described below with reference to FIG. 1, etc., are realized by the CPU 701 reading the program 708 stored in the storage device 703 and executing the program. Note that some or all of the functions of the image processing apparatus 100 described below with reference to FIG. 1, etc., may be realized by dedicated hardware. The input-output interface 704 is connected to an operating unit 160 and a display unit 170. The network interface 709 connects the image processing apparatus 100 and the network 130.

FIG. 1 illustrates the functional configuration of the image processing apparatus according to the first embodiment. As described above with reference to FIG. 7, the image processing apparatus 100 according to the first embodiment is connected to the data server 150, the operating unit 160, and the display unit 170.

The three-dimensional image stored in the data server 150 is a three-dimensional tomographic image acquired by preliminarily capturing images of a subject using the X-ray CT apparatus 120. Note that the three-dimensional tomographic image includes a set of two-dimensional tomographic images, and the position and orientation of each of the two-dimensional tomographic images are converted into a reference coordinate system (a coordinate system in a space based on the subject) and stored in the data server 150. The three-dimensional image represented by the reference coordinate system is input to the image processing apparatus 100 via an image acquisition unit 102. The operating unit 160 accepts input of an operation made by a user on a mouse or a keyboard for inputting a parameter (for example, slab thickness) of projection processing, under the control of the parameter acquisition unit 104. The display unit 170 displays a display image generated by the image processing apparatus 100, under the control of a display controller 110. Moreover, the display unit 170 is also provided with a GUI for acquiring an instruction from the user.

The image acquisition unit 102 of the image processing apparatus 100 acquires a three-dimensional image (original image) from the data server 150. The parameter acquisition unit 104 acquires a parameter of projection processing in accordance with an instruction from the user received by the operating unit 160. An image processor 106 performs image processing on the three-dimensional image and calculates the processed three-dimensional image. Moreover, the image processor 106 acquires the parameter of projection processing from the parameter acquisition unit 104 and determines, on the basis of the parameter, the parameter of image processing. Details of the processing will be described in the description of step S202. An image projector 108 acquires the parameter of projection processing from the parameter acquisition unit 104, projects the three-dimensional image processed by the image processor 106 on the basis of this parameter, and calculates a two-dimensional projection image. Details of this processing will be described in the description of step S204. The display controller 110 displays, on the display unit 170, the two-dimensional projection image calculated by the image projector 108.

FIG. 2 is a flowchart illustrating the procedure of an image processing method carried out by the image processing apparatus 100. In step S200, the image acquisition unit 102 acquires a three-dimensional image of a subject from the data server 150, and outputs the acquired three-dimensional image to the image processor 106 and the display controller 110. In step S201, the parameter acquisition unit 104 acquires a slab projection parameter in accordance with an instruction from a user. In the first embodiment, the slab projection parameter includes a projection direction vector, the thickness of a projection range (slab thickness), and the coordinates of the central position of the projection range.

An example of a method of acquiring a slab projection parameter will now be described. Now, assume that one slice image of the three-dimensional image acquired in step S200 is displayed on the display unit 170. It is assumed that this display image can be changed to a cross-sectional image at any position along any cross-sectional direction in accordance with an instruction from a user. The user searches for a position that is to be the center of the projection calculation while shifting the slice, enlarging/reducing the image, and changing the cross-sectional direction. After the position that is to be the center of the projection calculation has been determined, the slab thickness is input to a textbox displayed on the display unit 170. For example, a value, such as 3.0 mm, is input. In such a case, a direction orthogonal to the slice of the currently displayed cross-sectional slice is the direction of the projection direction vector; the central position of the currently displayed display image is the coordinates of the central position of the projection range; and the value input to the textbox is the slab thickness. These values are input to the image processing apparatus 100 as slab projection parameters.

Next, in step S202, the image processor 106 determines image processing parameters on the basis of a slab projection parameter acquired in step S201. In this embodiment, the slab projection parameter used in step S202 is the slab thickness. Furthermore, in the first embodiment, the image processing applied to the three-dimensional image in step S203 is low-density-region reduction processing for reducing the density of the surrounding region in the three-dimensional image, as described above. In step S202, the image processor 106 determines a parameter for controlling the intensity of reduction or enhancement of a predetermined density region in the low-density-region reduction processing.

Figure 3B:
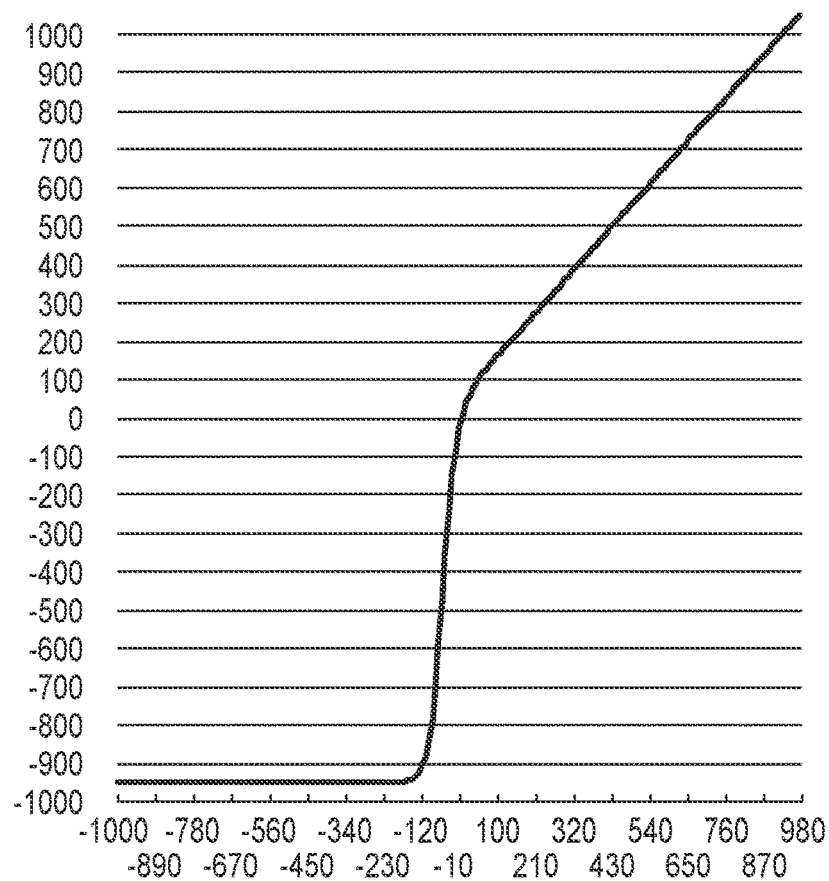
FIG. 3B is a diagram illustrating a density-value conversion function during low-density-region reduction processing.

Before describing the image processing parameters calculated in step S202, low-density-value-region reduction processing will be described with reference to FIGS. 3A and 3B. FIGS. 3A and 3B illustrate graphs representing density-value conversion in low-density-region reduction processing. In FIGS. 3A and 3B, the horizontal axis represents the density values in the original image, and the vertical axis represents the density values in the processed result image. FIG. 3A represents a case prior to density-value conversion, i.e., no conversion. On the other hand, FIG. 3B illustrates a graph representing density-value conversion with low-density-region reduction processing. The density value conversion illustrated in FIG. 3B is represented by the following Expression 1.

$$y = x_{min} + (x - x_{min}) \times \frac{1}{1 + \exp(-\alpha \times (x - s_{th}))} \quad \text{[Expression 1]}$$

Here, x and y are the density values before and after density-value conversion, $\alpha$ is a coefficient for controlling the slope of the density-value conversion coefficient, and $s_{th}$ is a reduction density threshold that determines the threshold of the density value to be reduced. Moreover, $x_{min}$ is the minimum density value when a density value is to be reduced, and in the case of a CT image, this value is $-1000$, i.e., a density value equivalent to an air region. That is to say, Expression 1 defines density-value conversion performed by weighting the density value of the original image on the basis of a sigmoid function. FIG. 3B represents a case in which $\alpha=0.05$ and $s_{th}=-50$.

The image processing parameters that are the target of calculation in step S202 are $\alpha$ (coefficient for controlling the slope) and $s_{th}$ (reduction density threshold) in Expression 1. In this embodiment, when the slab thickness is larger than a predetermined value (5.0 mm in this case), low-density-region reduction processing is performed with $\alpha=0.05$ and $s_{th}=-50$. In contrast, when the slab thickness is smaller than or equal to the predetermined value, the parameters are set so that substantially no low-density reduction processing is performed (for example, $\alpha=0.0$ and $s_{th}<<-1000$). Note that, when the slab thickness is smaller than or equal to the predetermined value or when a slice is to be displayed, the processing may be switched so as to not carry out low-density reduction processing on the three-dimensional image. In such a case, the three-dimensional image not yet subjected to image processing is used for projection processing and display of the projection image, or display of a slice.

Note that, in the first embodiment, "application/non-application" of low-density-region reduction processing changes at a slab thickness of 5.0 mm, but this value is an example and can be changed to a suitable value corresponding to the subject or the image. Furthermore, the parameters ($\alpha=0.05$ and $s_{th}=-50$) of the low-density-region reduction processing are also examples, and can be changed to suitable values corresponding to the subject or the image.

In the first embodiment, a case of switching of the low-density-region reduction processing between "applied" and "not applied" in accordance with the slab thickness has been described as an example, but the parameters of the low-density-region reduction processing may be continuously varied according to the slab thickness. In such a case, when the slab thickness is a predetermined value (for example, 5.0 mm), $\alpha=0.0$ and $s_{th}=-1000$, whereas when the slab thickness is another predetermined value (for example, 15.0 mm), $\alpha=0.05$ and $s_{th}=-50$. The two types of parameters are then set to values that linearly connect the slab thickness from 5.0 to 15.0 mm. In this way, the intensity of low-density-region reduction processing can be increased as the thickness (slab thickness) of the projection range increases in projection processing, and thereby a decrease in contrast in the projection image due to an increase in the slab thickness can be effectively corrected.

In step S203, the image processor 106 uses the image processing parameters calculated in step S202 and applies image processing to the three-dimensional image acquired in step S200. As described in step S202, the image processing according to the first embodiment is low-density-region reduction processing.

Figure 4A:
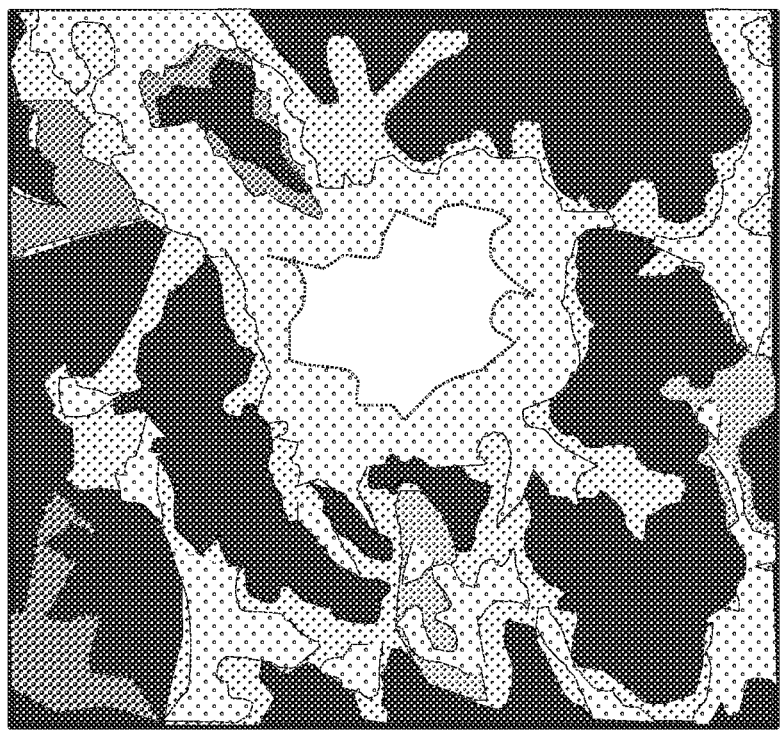
FIG. 4A is a schematic diagram illustrating a processing result of low-density-region reduction processing.
Figure 4B:
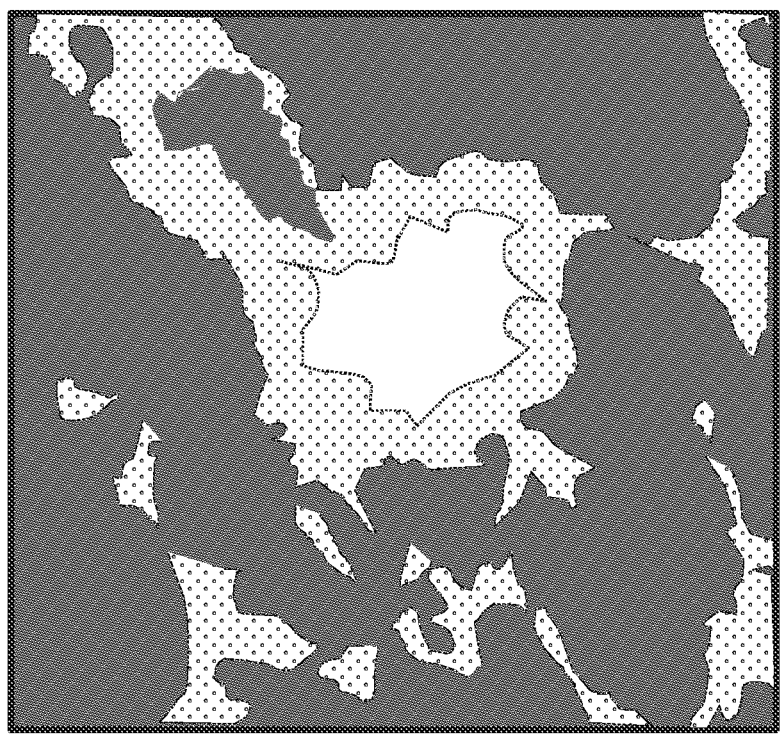
FIG. 4B is a schematic diagram illustrating the processing result of low-density-region reduction processing.

The effect of low-density-region reduction processing according to this embodiment will be described with reference to FIGS. 4A and 4B. FIGS. 4A and 4B schematically illustrate a tumor region and its vicinity in a three-dimensional CT image capturing a breast region, in which FIG. 4A illustrates a tumor region before application of image processing, and FIG. 4B illustrates the tumor region after application of image processing. According to FIG. 4A, a tumor region exists near the center of the image, and a mammary gland region exists in the surrounding region of the tumor region. The tumor region is a blob-shaped structure region having a substantially spherical shape and a large density value, and the mammary gland region is a linear structure having a density value similar to that of the tumor region. The tumor region and the mammary gland region float in a fat region, which is indicated by a dark gray color in FIG. 4A. Low-density-region reduction processing is a process for converting an image such as that illustrated in FIG. 4A to an image such as that illustrated in FIG. 4B. That is, it is processing in which regions having density values larger than a predetermined value are not processed while regions having density values smaller than or equal to the predetermined value are reduced to a low density (in the case of a CT image, −1000, which is a CT value representing an air region). Here, it should be noted that this processing differs from binarization. That is, since regions having density values larger than the predetermined value are not processed, regions having large density values have the same gray values as those of the original image.

In step S204, the image projector 108 performs image projection processing using the slab projection parameters acquired in step S201 (the coordinates of the central position of the range in which the projection calculation is to be performed, the projection direction vector, and the thickness of the range in which projection is to be performed (slab thickness)), and calculates a projection image. As described above, in this embodiment, a ray summation projection method (RaySum projection), which is a known projection technique, is used as the image projection technique.

RaySum projection that uses the slab thickness will now be described. When the slab thickness is used for normal projection processing that defines the entire region of the three-dimensional image as a calculation target, projection processing with a limited region is carried out. That is, the coordinates of the central position of the range in which projection calculation is to be carried out are established as the origin of the projection calculation, and, in the vicinity of the origin, the range corresponding to "±slab thickness/2" in the projection direction is defined as the calculation range of projection processing. In this way, the range to be used as a calculation target of projection processing can be limited to the target range.

In step S205, the display controller 110 controls the display unit 170 to display the projection image calculated in step S204.

As described above, the first embodiment has an effect in which, even when the slab thickness is large, a projection image having an enhanced contrast can be calculated through RaySum projection processing, and a three-dimensional image can be read with ease.

Modification 1-1

In the first embodiment, a case is described as an example in which low-density-region reduction processing is carried out when the slab thickness in the projection display is larger than a predetermined value, and low-density-region reduction processing is not carried out when the slab thickness is smaller than or equal to the predetermined value. That is, described is a configuration for changing between carrying out or not carrying out low-density-region reduction processing depending on the slab thickness. However, the configuration for switching between carrying out and not carrying out low-density-region reduction processing is not limited to this. For example, a configuration may be employed in which switching between carrying out and not carrying out low-density-region reduction processing depends on whether projection display is to be carried out. For example, when projection display is not to be carried out, no low-density-region reduction processing is carried out, and when projection display is to be carried out, low-density-region reduction processing is carried out regardless of the slab thickness.

In such a case, prior knowledge, such as "examination of a projection image subjected to image processing is facilitated when the slab thickness is larger than XX mm" is not required as a condition for determining whether to carry out image processing. Therefore, there is an effect in which the present technology is applicable without depending on the type of subject.

Modification 1-2

In the first embodiment, an example has been described in which the image processing carried out by the image processor 106 is low-density-region reduction processing, and the projection processing carried out by the image projector 108 is RaySum projection, but an image processing technique and a projection technique besides these may be used. For example, a configuration may be employed in which blob-shaped structure enhancement and linear structure reduction are used in image processing of a three-dimensional image, and maximum intensity projection (MIP), which is a known projection technique, is used in projection processing.

MIP is a projection technique in which the maximum density value on a projection path is defined as the density value of the corresponding pixel in a two-dimensional projection image. Unlike RaySum projection in which the contrast between a target region and a non-target region tends to decrease with an increase in the slab thickness, MIP can clearly depict the outline of the target region if the density value of the target region is large. On the other hand, MIP has the problem of being highly susceptible to noise. In the case of a breast CT image exemplified in this embodiment, a "mammary gland region", which has a density as high as that of the tumor region and has a linear structure, often exists in the surrounding region of the tumor region, which is the target region. Therefore, there is a problem in that the tumor region is buried in the mammary gland region and is difficult to examine.

Modification 1-2 solves the above-described problem by enhancing the tumor region and reducing the mammary gland region through image processing. As a known technique, there is a known technique for determining whether a local region in an image has a structure similar to a blob-shaped structure, a linear structure, or a sheet-shaped structure on the basis of an eigenvalue of a matrix of second-order partial derivatives (Hessian matrix) of the image density values (NPL 1). The image processing in modification 1-2 extracts a blob-shaped structure region and a linear structure region in a three-dimensional image using, for example, the known technique. In a breast CT image, which is a target in this embodiment, the blob-shaped structure region corresponds to a tumor region (the target region in the first embodiment), and the linear structure region corresponds to a mammary gland region (the non-target region in the first embodiment). The blob-shaped structure region is enhanced, i.e., the density values are increased, and the linear structure region is reduced, i.e., the density values are decreased. Such image processing is applied when the slab thickness of MIP is larger than or equal to a predetermined value.

According to modification 1-2, since the density values of regions other than the target region (tumor region) are reduced through image processing, there is an effect in that, when MIP is used as the projection technique, compatibility can be established between the clarity of the visualization of the outline of the target region and the ease of examining the target region.

Modification 1-3

In the first embodiment, a case in which parameters are set interactively through the use of a GUI application has been described (step S201), but any setting method can be used so long as the three types of parameters (slab projection parameters) described in the first embodiment can be established. For example, a target region is automatically extracted using a known technique, such as a blob-shaped structure enhancement filter using an eigenvalue of a Hessian matrix, which is disclosed in NPL 1. The projection direction, the slab thickness, and the coordinates of the central position (the three types of parameters) may be automatically established so as to sufficiently include the extraction range. In this way, the user does not have go through the trouble of manually setting the parameters for projection processing.

Modification 1-4

In the first embodiment, a case in which an image of a subject is captured by the X-ray CT apparatus 120 has been described, but the application of the present invention is not limited to an X-ray CT apparatus. For example, any one of various modalities such as an MRI apparatus, a dimensional ultrasonic imaging apparatus, a photoacoustic tomography apparatus, a PET/SPECT apparatus, and an OCT apparatus may be used.

Second Embodiment

Figure 5:
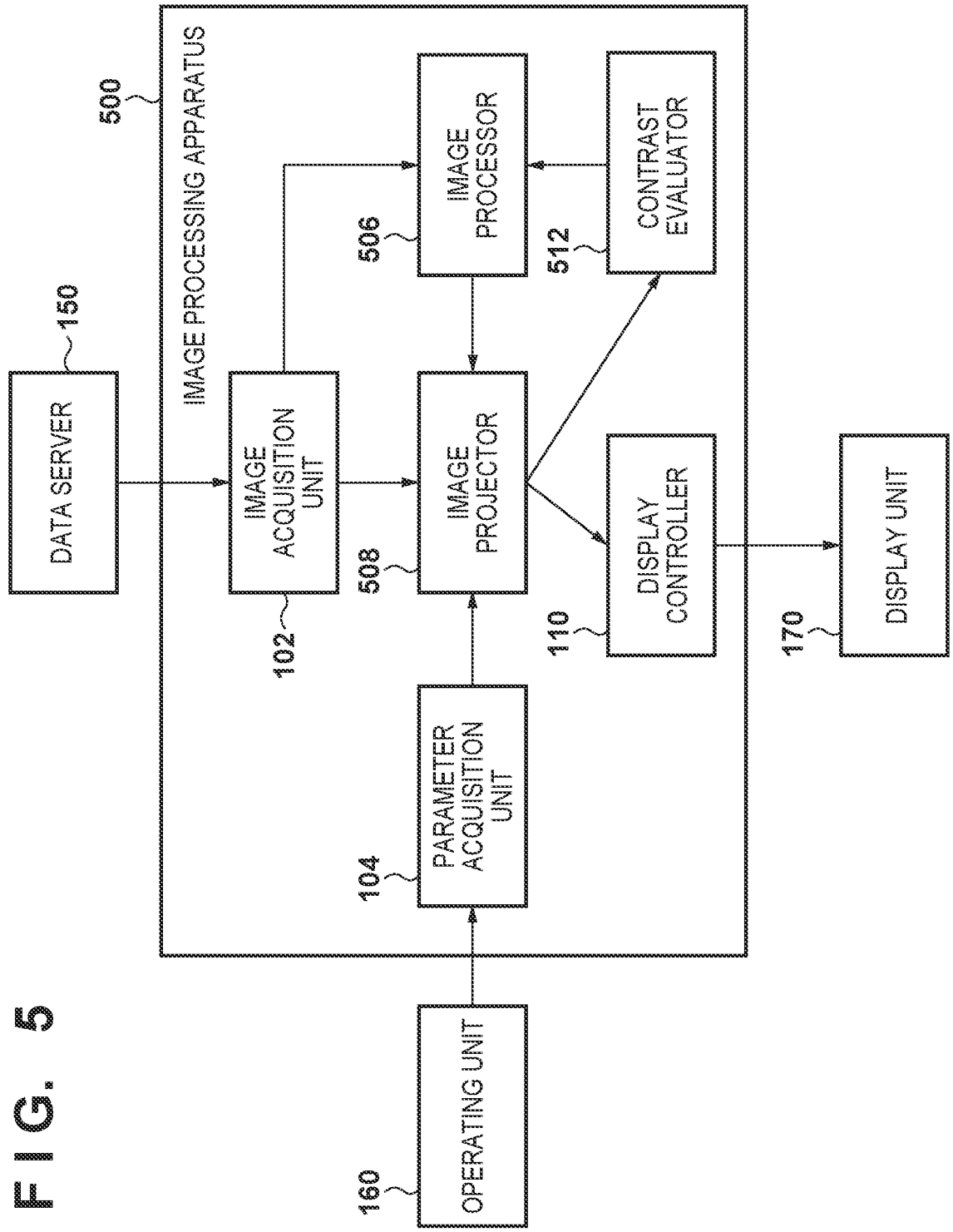
FIG. 5 is a block diagram illustrating a functional configuration example of an image processing apparatus according to a second embodiment.

In the first embodiment, a case in which parameters for the image processing are calculated on the basis of the slab thickness, which is one of the image projection parameters, has been described as an example. In contrast, an image processing apparatus according to the second embodiment calculates parameters of image processing on the basis of feature amounts, not image projection parameters, calculated from a two-dimensional projection image. Specifically, parameters of image processing for a three-dimensional image are calculated on the basis of the contrast in a two-dimensional projection image. FIG. 5 illustrates the configuration of an image processing system according to the second embodiment. Components that are common with those of the first embodiment are denoted by the same reference numerals as those in FIG. 1. Note that, in the second embodiment, a case in which low-density-region reduction processing is used as image processing, as in the first embodiment, will be described as an example.

In the image processing apparatus 100, an image processor 506 receives a three-dimensional image acquired by the image acquisition unit 102 and a determination result of "whether or not the contrast of a two-dimensional projection image is larger than a predetermined value" calculated by a contrast evaluator 512. The image processor 506 then calculates parameters of image processing on the basis of the determination result, and executes image processing on the three-dimensional image using the calculated parameters of image processing. Details of the processing executed by the image processor 506 will be described in the description of step S604.

An image projector 508 receives the three-dimensional image of a subject acquired by the image acquisition unit 102 (original image) or the three-dimensional image subjected to image processing by the image processor 506 (processing result image), and receives image projection parameters acquired by a parameter acquisition unit 104. The image projector 508 then calculates a two-dimensional projection image based on the received data, and outputs the calculated two-dimensional projection image to a display controller 110 and the contrast evaluator 512. In comparison with the image projector 108 of the first embodiment, the image projector 508 differs in two points, namely that the input image may be the original image besides the processing result image, and the contrast evaluator 512 is added as an output destination, but the processing content is the same.

The contrast evaluator 512 receives the projection image calculated by the image projector 508, calculates the contrast value of the received projection image as a feature amount, and determines whether or not the calculated contrast value is larger than a predetermined value. The contrast evaluator 512 outputs the determined result to the image processor 506. Details of the processing executed by the contrast evaluator 512 will be described in the description of step S603.

Figure 6:
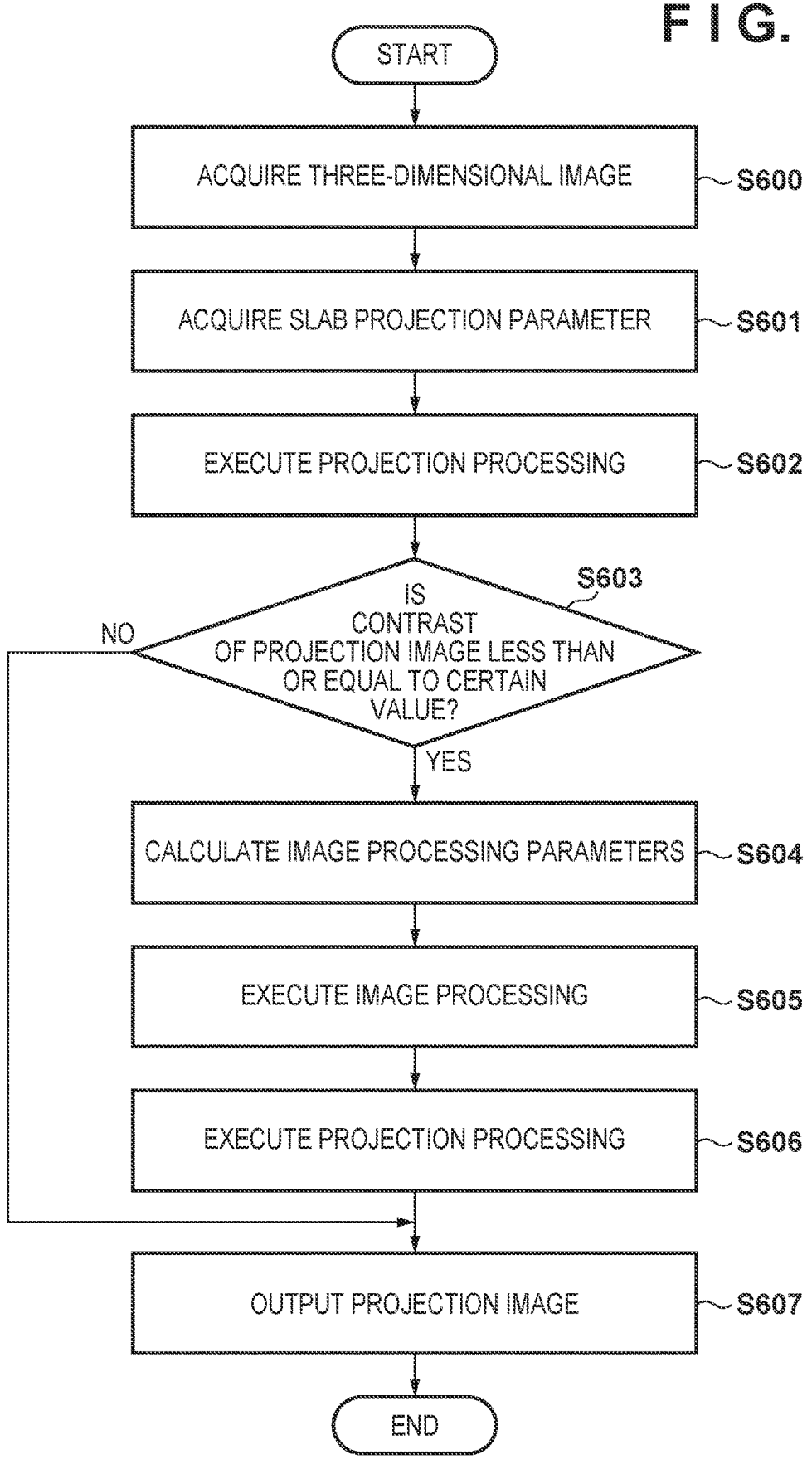
FIG. 6 is a flowchart illustrating an overall processing procedure according to the second embodiment.

FIG. 6 is a flowchart illustrating an example of a procedure of an image processing method performed by the image processing apparatus 100 in the second embodiment. Note that steps S600, S601, S605, and S607 share the same processing of steps S200, S201, S203, and S205 in FIG. 2, respectively. Moreover, steps S602 and S606 are the same as step S204 (execute projection processing) in FIG. 2. Thus, the descriptions of these processes are omitted.

In step S603, the contrast evaluator 512 calculates the contrast value of the two-dimensional projection image calculated by the image projector 508, and outputs information regarding whether or not the contrast value is larger than a certain value to the image processor 506. The contrast value is calculable using, for example, Michelson contrast, which is a known technique. That is, the contrast value is calculated using the following Expression 2.

$$C = \frac{L_{max} - L_{min}}{L_{max} + L_{min}} \qquad \text{[Expression 2]}$$

Here, C is the contrast value, and $L_{max}$ and $L_{min}$ are respectively the maximum density value and the minimum density value of the two-dimensional projection image. If the contrast value C is larger than a predetermined value (for example, 0.5), the contrast evaluator 512 determines that the contrast value C is "larger than the predetermined value," and if not, determines that the contrast value C is "smaller than or equal to the predetermined value".

Note that Expression 2 calculates the contrast value on the basis of the maximum density value and the minimum density value in the image. Thus, when noise of significantly high or low density is included in the image, the contrast may not be accurately calculated. To solve this problem, the image may be preliminarily smoothed using a known smoothing filter, such as a Gaussian filter, before the contrast value is calculated.

In step S603, if the contrast value is determined as being smaller than the predetermined value, the image processor 506 applies low-density-region reduction processing to the three-dimensional image of the subject (original image) acquired by the image acquisition unit 102 in step S604. The parameters of low-density-region reduction processing are $\alpha = 0.05$ and $s_{th} = -50$, as in the first embodiment.

Note that, here, a case in which image processing is carried out with predetermined parameters when the contrast value is smaller than or equal to the predetermined value is described as an example, but it is not limited to this. For example, the parameters of image processing may be optimized so as to gradually enhance the effect of image processing, until the contrast value exceeds the predetermined value. This is equivalent to optimizing the two parameters a and $s_{th}$ under the condition of increasing the contrast value C to be larger than the predetermined value. For optimization, it is possible to use a known repeated optimization technique, such as gradient descent and Powell's method.

As described above, according to the second embodiment, it is possible to calculate parameters of image processing by directly evaluating a two-dimensional projection image, in place of the parameters input for the calculation of the two-dimensional projection image.

Note that, in the second embodiment, while whether image processing is to be executed or not by the image processor 506 is determined on the basis of the evaluation of the contrast value of the projection image, it is not limited to this. The parameters related to image processing on a three-dimensional image may be determined by acquiring a feature amount other than the contrast from a projection image acquired from an input three-dimensional image and evaluating a feature amount other than the contrast. For example, a projection image may be subjected to processing for determining the structure as being a blob-shaped, linear, or sheet-shaped structure, as disclosed in NPL 1, and thereby "blob-likeness" may be acquired as a feature amount of the projection image. In such a case, whether or not the current target region is similar to a blob-shaped structure region (for example, a tumor region in the case of a breast CT image) may be evaluated, so as to determine whether or not to execute image processing. Furthermore, multiple types of feature amounts may be acquired from the acquired projection image, and whether or not to execute image processing (low-density-region reduction processing) may be switched on the basis of the feature amounts.

As described above, the embodiments can provide an image processing apparatus that enhances the visibility of an image generated from a three-dimensional image.

Other Embodiments

Although the embodiments have been described above in detail, the present invention may be embodied in a system, an apparatus, a method, a program, a storage medium, or the like. Specifically, the present invention may be applied to a system including multiple apparatuses by dispersing the functions of the image processing apparatus, or may be applied to an apparatus including a single device.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a memory storing a program; and
one or more processors which, by executing the program, function as a plurality of units comprising:
(1) a first acquiring unit configured to acquire a first three-dimensional image;
(2) an image processing unit configured to generate a second three-dimensional image by subjecting the first three-dimensional image to image processing; and
(3) a projecting unit configured to generate a two-dimensional projection image by subjecting the second three-dimensional image to projection processing,
wherein a parameter related to the projection processing of the projecting unit includes a thickness of a projection range of the projection processing,
wherein the image processing unit determines a parameter of the image processing based on the thickness of the projection range of the projection processing, and
wherein the image processing unit generates the second three-dimensional image by subjecting the first three-dimensional image to the image processing using the determined parameter of the image processing.

2. The image processing apparatus according to claim 1, wherein the image processing comprises gradation processing for reducing or enhancing a predetermined density region, and
wherein the image processing unit determines a parameter for controlling an intensity of reduction or enhancement of the predetermined density region in the gradation processing.

3. The image processing apparatus according to claim 2, wherein the projection processing comprises ray summation projection.

4. The image processing apparatus according to claim 2, wherein the intensity of the reduction or the enhancement of the predetermined density region increases with an increase in a thickness of a projection range of the projection processing indicated by the parameter related to the projection processing.

5. The image processing apparatus according to claim 1, wherein the image processing comprises (1) one of (a) a first process of reducing or enhancing a blob-shaped structure in an image and (b) a second process of reducing or enhancing a linear structure in an image, or (2) a combination of the first image process and the second image process.

6. The image processing apparatus according to claim 5, wherein the image processing unit enhances the blob-shaped structure and reduces the linear structure.

7. The image processing apparatus according to claim 5, wherein the projection processing comprises maximum intensity projection.

8. The image processing apparatus according to claim 1, wherein the image processing of the image processing unit is executed when a thickness of a projection range of the projection processing indicated by the parameter related to the projection processing is larger than a predetermined value, and wherein the image processing of the image processing unit is not executed when the thickness of the projection range is smaller than or equal to the predetermined value.

9. The image processing apparatus according to claim 1, wherein the plurality of units further comprises a display controlling unit configured to display a projection image generated by the projecting unit on a display unit.

10. An image processing apparatus comprising:
a memory storing a program; and
one or more processors which, by executing the program, function as a plurality of units comprising:
(1) a first acquiring unit configured to acquire a first three-dimensional image;
(2) a projecting unit configured to generate a first projection image by subjecting the first three-dimensional image to projection processing; and
(3) an image processing unit configured to generate a second three-dimensional image by subjecting the first three-dimensional image to image processing,
wherein the image processing unit determines a parameter related to the image processing performed on the first three-dimensional image based on a feature amount calculated from the first projection image, and
wherein the image processing unit generates the second three-dimensional image by subjecting the first three-dimensional image to the image processing using the determined parameter related to the image processing.

11. The image processing apparatus according to claim 10, wherein the projecting unit generates a two-dimensional second projection image by subjecting the second three-dimensional image to projection processing.

12. The image processing apparatus according to claim 10, wherein the image processing unit determines whether or not to execute the image processing based on a feature amount of the first projection image.

13. The image processing apparatus according to claim 10, wherein the feature amount includes a contrast value of the first projection image.

14. The image processing apparatus according to claim 10, wherein the feature amount includes a contrast value of the first projection image, and
wherein the image processing unit (a) executes the image processing when the contrast value is smaller than or equal to a predetermined value and (b) does not execute the image processing when the contrast value is larger than the predetermined value.

15. The image processing apparatus according to claim 14, wherein the feature amount includes a contrast value of the first projection image, and
wherein the image processing unit enhances an effect of the image processing to increase the contrast value to be larger than the predetermined value when the contrast value is smaller than or equal to the predetermined value.

16. An image processing method for processing a three-dimensional image, the method comprising:
acquiring a first three-dimensional image;
generating a second three-dimensional image by subjecting the first three-dimensional image to image processing; and
generating a two-dimensional projection image by subjecting the second three-dimensional image to projection processing,
wherein a parameter related to the projection processing includes a thickness of a projection range of the projection processing, wherein, in the generating the second three-dimensional image, (a) a parameter of the image processing is determined based on the thickness of the projection range of the projection processing, and (b) the second three-dimensional image is generated by subjecting the first three-dimensional image to the image processing using the determined parameter of the image processing.

17. A non-transitory computer-readable medium storing a program for causing a computer to execute the image processing method according to claim 16.

18. An image processing method for processing a three-dimensional image, the method comprising:

acquiring a three-dimensional image;

generating a projection image by subjecting the three-dimensional image to projection processing; and generating a second three-dimensional image by subjecting the first three-dimensional image to image processing, wherein a parameter related to the image processing performed on the three-dimensional image is determined based on a feature amount calculated from the projection image, and wherein the second three-dimensional image is generated by subjecting the first three-dimensional image to the image processing using the determined parameter related to the image processing.

19. A non-transitory computer-readable medium storing a program for causing a computer to execute the image processing method according to claim 18.

20. An image processing apparatus comprising:

a memory storing a program; and one or more processors which, by executing the program, function as a plurality of units comprising:

(1) a first acquiring unit configured to acquire a first three-dimensional image;

(2) an image processing unit configured to generate a second three-dimensional image by subjecting the first three-dimensional image to image processing; and (3) a projecting unit configured to generate a two-dimensional projection image by subjecting the second three-dimensional image to projection processing, wherein the image processing unit determines a parameter of the image processing based on a parameter related to the projection processing of the projecting unit, wherein the image processing of the image processing unit is executed when a thickness of a projection range of the projection processing indicated by the parameter related to the projection processing is larger than a predetermined value, and wherein the image processing of the image processing unit is not executed when the thickness of the projection range is smaller than or equal to the predetermined value.

* * * * *